US007507145B1

(12) United States Patent
Zurbuchen

(10) Patent No.: US 7,507,145 B1
(45) Date of Patent: Mar. 24, 2009

(54) AUTOMATED SECTIONING TOMOGRAPHIC MEASUREMENT SYSTEM

(75) Inventor: Mark A. Zurbuchen, Santa Monica, CA (US)

(73) Assignee: The Aerospace Corporation, El Segundo, CA (US)

( * ) Notice: Subject to any disclaimer, the term of this patent is extended or adjusted under 35 U.S.C. 154(b) by 0 days.

(21) Appl. No.: 11/904,656

(22) Filed: Sep. 28, 2007

(51) Int. Cl.
*B24B 49/00* (2006.01)

(52) U.S. Cl. .................. 451/6; 451/8; 451/10; 451/11; 451/278

(58) Field of Classification Search .............. 451/5, 451/6, 8, 10, 11, 41, 278, 280, 285, 287, 451/288; 438/16
See application file for complete search history.

(56) References Cited

U.S. PATENT DOCUMENTS

| | | | | |
|---|---|---|---|---|
| 5,191,738 A | * | 3/1993 | Nakazato et al. | 451/41 |
| 5,305,559 A | * | 4/1994 | Ogawa | 451/54 |
| 6,524,163 B1 | * | 2/2003 | Stirton | 451/5 |
| 6,533,641 B1 | * | 3/2003 | Morken et al. | 451/6 |
| 7,014,531 B2 | * | 3/2006 | Hansen | 451/8 |
| 2002/0001761 A1 | * | 1/2002 | Mizutani et al. | 430/5 |
| 2002/0081440 A1 | * | 6/2002 | Murakami et al. | 428/446 |
| 2002/0090799 A1 | * | 7/2002 | Vepa et al. | 438/459 |
| 2002/0182986 A1 | * | 12/2002 | Tung et al. | 451/56 |
| 2003/0060127 A1 | * | 3/2003 | Kaushal et al. | 451/8 |
| 2004/0185752 A1 | * | 9/2004 | Han | 451/8 |
| 2008/0159697 A1 | * | 7/2008 | Lu | 385/85 |

* cited by examiner

Primary Examiner—Eileen P. Morgan
(74) Attorney, Agent, or Firm—Derrick Michael Reid

(57) ABSTRACT

A tomographic system includes a reporting device colocated and juxtaposed an object so that both are ground through grinding to various sectioning depths as the reporting device is ground down exposing a reporting marker along a length of the reporting device for indicating the depth of sectioning for accurate precise depth of grinding well suited for precise sectioned tomographic imaging.

16 Claims, 3 Drawing Sheets

REPORTING TOMOGRAPHY PROCESS

AUTOMATED TOMOGRAPHY SYSTEM

REPORTING DEVICE

REPORTING TOMOGRAPHY PROCESS

AUTOMATED SECTIONING TOMOGRAPHIC MEASUREMENT SYSTEM

FIELD OF THE INVENTION

The invention relates to the field of tomography. More particularly, the present invention relates to grinding, polishing, and imaging of objects in sliced sections.

BACKGROUND OF THE INVENTION

There is frequently a need to image the internal, three-dimensional structure of objects, in order to analyze internal structures or mechanism of failure, particularly at the scale from 200 nm to 10 mm. Imaging methods based on the transmission of a probe beam through a material can be used to generate a tilt series of data for three dimensional reconstruction, but such methods are typically insensitive to structure parameters, and are limited in the resolution that can be provided. A potentially more informative and higher spatial resolution approach to the collection of tomographic data sets can be to physically section an object in many slices while collecting images at incremental sectioning steps through the object. This sectioning approach also enables the collection of maps of many structure parameters, such as composition, orientation, hardness, and resistivity. Further, surface treatments known to reveal microstructural information can be used at each step, expanding the range of structure parameters that can be mapped for each slice sectioning an object, and thus, for the entire object being examined.

A straightforward approach to sectioning an object for tomography is the mechanical removal of material of each slice to be imaged, known as serial sectioning. A major problem exists with the sectioning approach. For the mechanical sectioning approach, however, it is very difficult to accurately measure the depth of any particular step of material removal at small length scales. This is in part caused by the difficulty in maintaining a reference plane for an object being sectioned in a planar manner. Mechanical measurement systems that do not rely on a reference plane on the object being measured are limited to a resolution of one micron at best, rendering the sectioning only useful for objects with detail on the scale of at least twenty microns. That is, objects that are least two centimeters in size, or larger, can be mechanically sectioned with good resolution.

Other methods of mechanical measurement, such as surface profilometry, measure only relative changes in height, and therefore require a reference plane if absolute depth measurements are desired. The profilometry method is not practical when sectioning an object in a planar manner. Other mechanical systems allow automated removal of material from an object by cutting or grinding, controlling the advance of a machining head. These removal methods are designed to reach and reveal a certain location within an object. The accuracy of these removal methods is severely limited to five microns in resolution. Interferometry methods enable measurement of depths with a much finer resolution, but such interferometry systems require an external reference object to measure the amount of material that has been removed from an object. As such, the interferometry methods suffer from the need to have external references. Additionally, incorporation of an interferometry system into an automated sectioning or tomography system would add significant complexity and cost.

Commercial companies offer systems that automate some process steps in a sectioning process. Such systems typically use a robotic arm to iterate between sectioning, cleaning, and imaging, with the sectioning steps lasting for a predetermined period of time. Such automated systems and methods reduce labor but are limited in resolution accuracy while sectioning through material. For example, sectioning rates are approximated, and typically a human operator must tend the machine in order to stop the sectioning process when the desired region is observed in the transient displayed images generated during the process. In some cases, the feature of interest will have an appearance that is characteristic enough to allow for the robotic sectioning apparatus to stop automatically, but with most objects, such is not the case. It is desirable to have a more predictably automated system that can accurately determine depths of sectioning.

Sectioning machines are available that are capable of accurately sectioning material, but with a precision of only five microns, which is too coarse for many applications. Such sectioning hardware relies on mechanical sensors to measure depth. The sectioning machines can store data on material removal rates and sectioning headwear rates to compensate for tool wear and drift. This offers an improvement over the measurement of only the depth of material removed, but is limited because such compensation requires calibration runs and to generate data sets related to tool wear and material grinding rates. It is necessary to perform these calibration runs before sectioning any new object that differs substantially from any performed previously on an instrument. Also, replacement of consumables such as the sectioning head requires recalibration. The frequent need for recalibration severely limits the use of such sectioning machines for sectioning objects and necessitates a thorough and complicated set of calibration data retention and labeling.

Several US patents describe methods of detecting end points of depth sectioning procedures and methods of measuring the depth of material removal in grinding and polishing operations. U.S. Pat. No. 7,014,531 describes a detection mark that is intended to measure the depth of grinding at a given stage. Its precision is five microns, which is insufficient for tomography of objects less than 1000 microns in size. U.S. Pat. No. 6,734,427 describes a method that uses an object of predetermined size to mark a stopping point for a polishing operation. It does not measure the increment of polishing steps. U.S. Pat. No. 6,533,641 describes a similar resolution capability and involves mounting a sample on a steep incline and imaging during grinding and polishing. The ground and polished surface is not imaged, rather the incline is merely used to allow visual access to distinguishable features during grinding and polishing of the object. The incline in this patent is intended to allow visual access to all surfaces of a parallelipipedal object during sectioning, and does not measure depth. U.S. Pat. No. 6,121,147 discloses a reporting substance for detecting a polishing depth, but suffers from two major limitations. First, the reporting substance marks only an end point in the grinding and polishing procedure. Second, the method describes the use of spectroscopy in detection, which leads to the use of overly complicated spectroscopy devices than are necessary for this application. U.S. Pat. No. 5,077,941 describes a predetermined pattern of raised bumps of known geometry as part of a sensor that can serve as a coarse indicator of depth during a grinding and polishing procedure. As various bump features becomes visible, the sectioning depth can be coarsely and qualitatively estimated. This method requires the building of a complicated reporting device as well. Prior sectioning and tomography systems and methods suffer from complicated and limited collateral reporting and sensing devices, and used the sectioned material as a sectioning object for measurement during grinding and polishing. These and other disadvantages are solved or reduced using the invention disclosed herein.

SUMMARY OF THE INVENTION

An object of the invention is to provide a tomographic system for sectioning an object in slices.

Another object of the invention is to provide a tomographic system for sectioning an object in slices using grinding processes.

Yet another object of the invention is to provide a tomographic system for accurate sectioning an object in slices using a reporting tool.

Still another object of the invention is to provide a tomographic system for accurate sectioning an object in slices using a reporting tool aligned in depth with the object.

A further object of the invention is to provide a tomographic system for sectioning an object in slices using grinding, polishing, and imaging processes.

A further object of this invention is to provide a system for the automation and integration of collection and 3D reconstruction of tomographic data to yield a 3D representation of a real object in the form of a computer file or graphical display.

The invention is directed to a tomographic system and method providing controlled accurate grinding and sectioning of objects using a reporting device. The reporting device enables accurate depth grinding while concurrently providing depth information during imaging of the object. The reporting device is colocated in depth and juxtaposed in plane for precise grinding control and object imaging. Being so juxtaposed and colocated, the reporting device can provide precise depth information within images of the object. The system includes a reporting device and grinding and polishing, rinsing and washing, and imaging stations that can be integrated for providing automated acquisition of depth values of images taken at various depths in a sectioning operation. The system enables the automated collection of three-dimensional tomography datasets accumulated by mechanically de-layering grinding of objects, for which the system provides a means of straightforward automated depth sensing. A simple edge-detection algorithm is sufficient for computer control software to recognize the reporting device reading in a given image. The reporting device can be used to stop the automated serial sectioning of objects at target depths.

In the preferred form, the reporting device comprising a planar film disposed in block having a bottom surface that is slanted so that the film is slanted in the depth dimension. The planar film is preferably a high-contrast coating sandwiched between a top and a bottom of the block. Being colocated and juxtaposed, the reporting device is ground in depth as is the object, revealing a reporting line that is a line across the planar film. As the grinding proceeds in depth, the reporting line appears in successive images to move across the block. The position of the reporting line across the block provides accurate information as to current depth of grinding of the reporting tool as well as the object being ground. Being colocated and situated juxtaposed to the object of interest, the planar film reports the progress of the grinding operation. When the reporting tool and the object are imaged together, for example, in between sectioning steps, the reporting tool can provide within the image a reference to the precise depth of the ground surface of the object.

As the object is progressively sectioned, that is ground down, the surface of the inclined reporting substance is progressively removed in a coplanar manner. A corresponding reporting line appears as a high-contrast marker in images and gives an indication corresponding to the depth of the section for enabling accurate measurement of the depth of material removed at all times during the operation. The reporting tool can be used to both control the grinding as well as reporting the ground depth. The reporting device is preferably used with an automated imaging and edge-detecting subsystem. Coupled with an automated sectioning system, the reporting devices can enable control of the rates and amounts of material removed from the object. The depth resolution of systems using the device can be as fine as 2.5 nm, two orders of magnitude greater than any other automated system commercially available. The invention covers a reporting device, which can be used to measure the depth and control grinding of every image in a series of images, including but not limited to the end point depth of the sectioning operation. These and other advantages will become more apparent from the following detailed description of the preferred embodiment.

DETAILED DESCRIPTION OF THE PREFERRED EMBODIMENT

Figure 1:
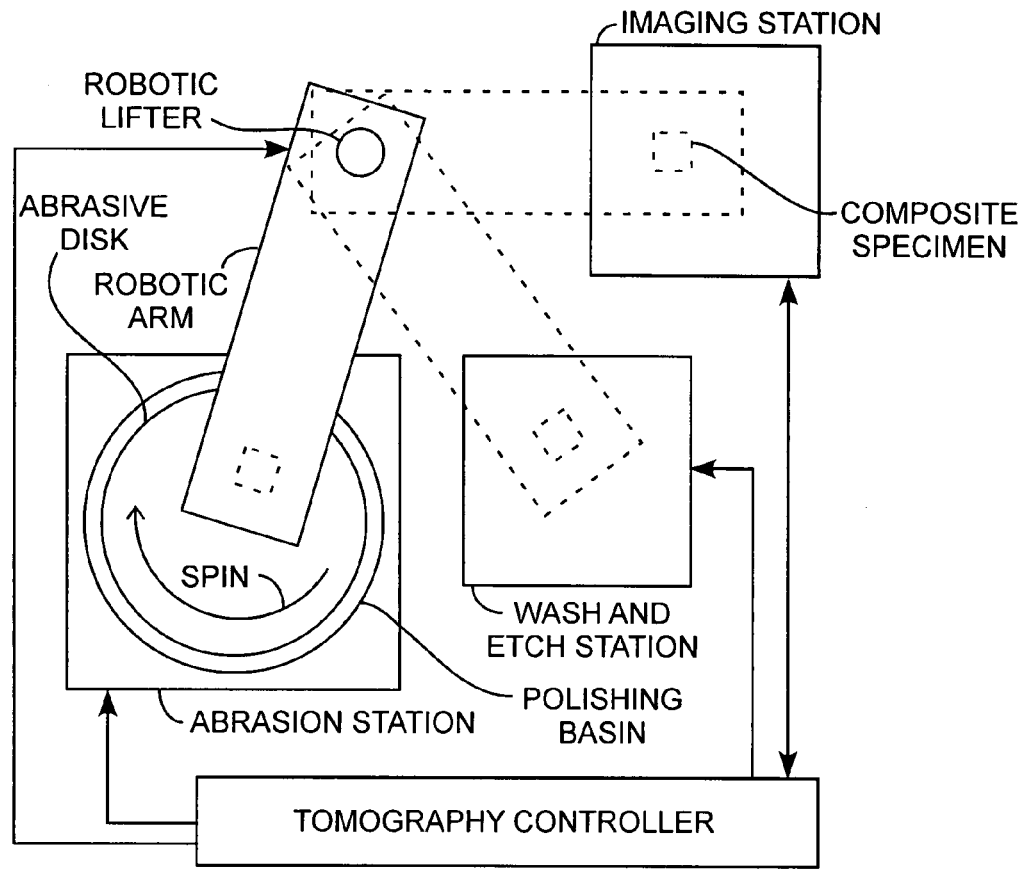
FIG. 1 is a block diagram of an automated tomography system.

An embodiment of the invention is described with reference to the figures using reference designations as shown in the figures. Referring to FIG. 1, an automated tomography system is used for grinding a composite specimen attached to a robotic lifter. The lifter moves the composite specimen between an abrasion station for grinding the specimen, a wash and (optional) etch station for washing, cleaning, and/or drying the specimen, and an imaging station for imaging the specimen. The abrasion station would include an abrasive disk having a grinding surface. The abrasive disk can provide various levels of grinding such as coarse, medium, and fine grinding depending on the size of the abrasive grit used. The abrasive disk can be made of any of the various grinding media such as diamond, aluminum oxide, silicon carbide, or others. A supporting substrate of the abrasive disk can be made of various materials used for that purpose, such as commercially available polyester films, cloth, glass plates, or metal bonds. The wash station has the function of removing grinding media, ground material, and lubricant from the specimen surface prior to imaging, where desired. While only one abrasion station, wash station, and image station are shown, the system could have any plural number of such stations. For example, the system could include three abrasion stations for coarse, medium, and fine grinding, along with respective wash stations, as desired. A tomography controller can be used to control the grinding, washing, imaging, and robotic movement of the specimen for creating a three dimensional data set of the object indexed to the sectioning depth. The controller can also be used for the computer processing of the image data into a 3D data cube for representation on a graphical display, or as a 3D computer file usable for further analysis.

Figure 2:
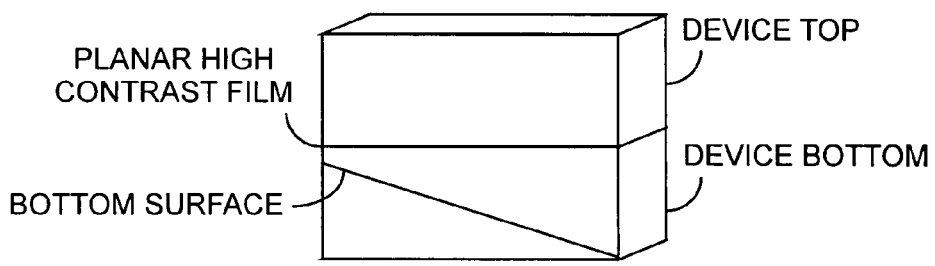
FIG. 2 depicts a reporting device.
Figure 3:
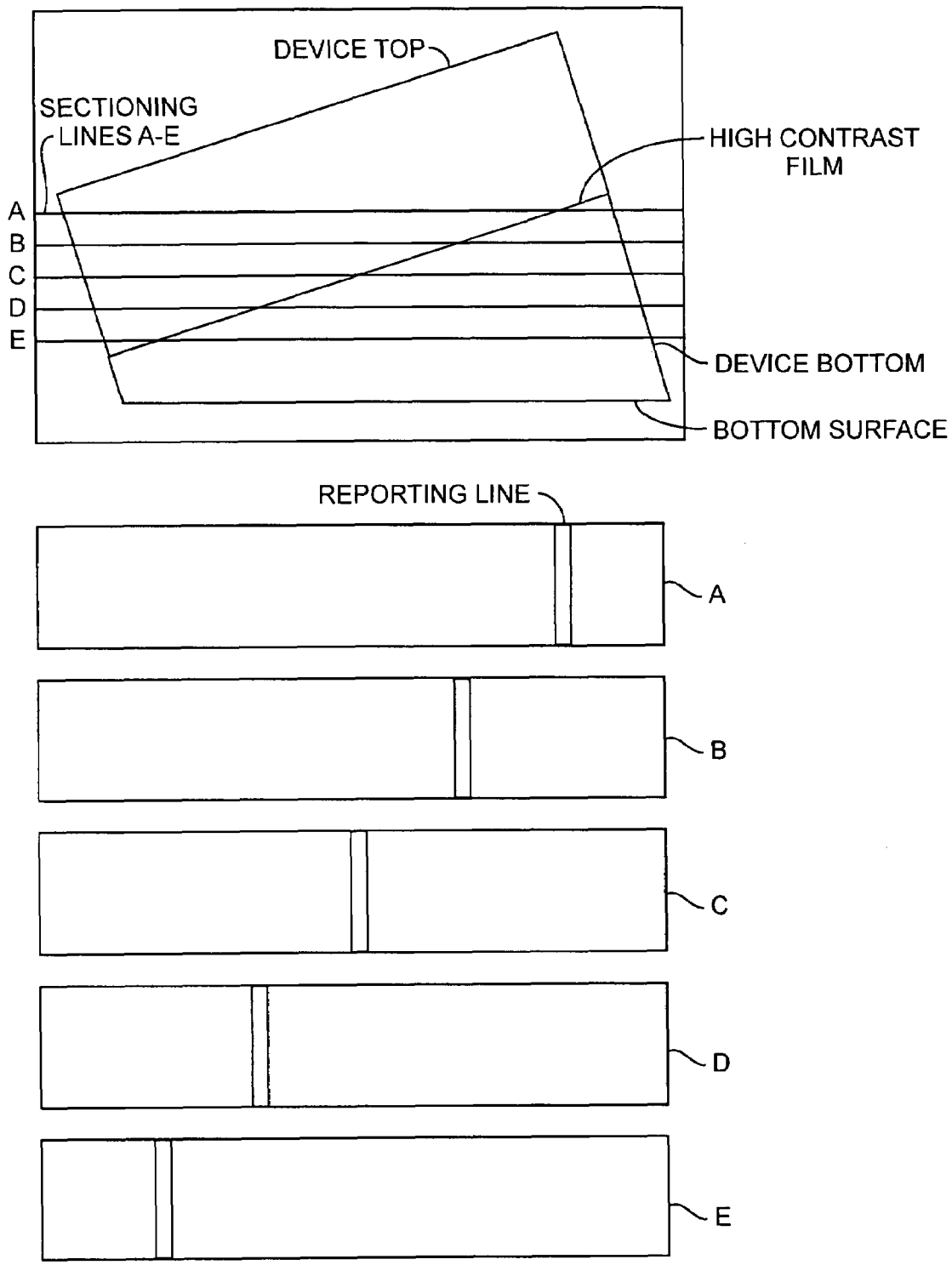
FIG. 3 shows a process flow of a processed reporting device.

Referring to FIGS. 1, 2, and 3, and more particularly to FIGS. 2 and 3, the composite specimen comprises a reporting device. The reporting is preferably a block having a device top and a device bottom, between which is disposed a planar high contrast film. The film is a layer having a predetermined thickness. The device bottom is then machined at a machining angle to provide the inclined bottom that concurrently inclines the planar high contrast layer. With such machining, the reporting device will rest at an incline as determined by the machined bottom surface of the reporting device. During grinding in the abrasive station, the reporting device is ground down from the top towards the bottom surface. In the exemplar processed reporting device is shown five sectioning lines A-E representing five different depths of grinding, that is, sectioning. As the grinding proceeds, the film is exposed and appears has a reporting line having a thickness that is related to the thickness of the film and the angle of the incline. As the grinding proceeds through sections A-E, the reporting line appears to move across the reporting device in successive images as the film is ground, such that, the position of the reporting line across the top ground surface of the reporting device visually and precisely indicates the depth of the sections in a linear manner with a high accuracy.

Figure 4:
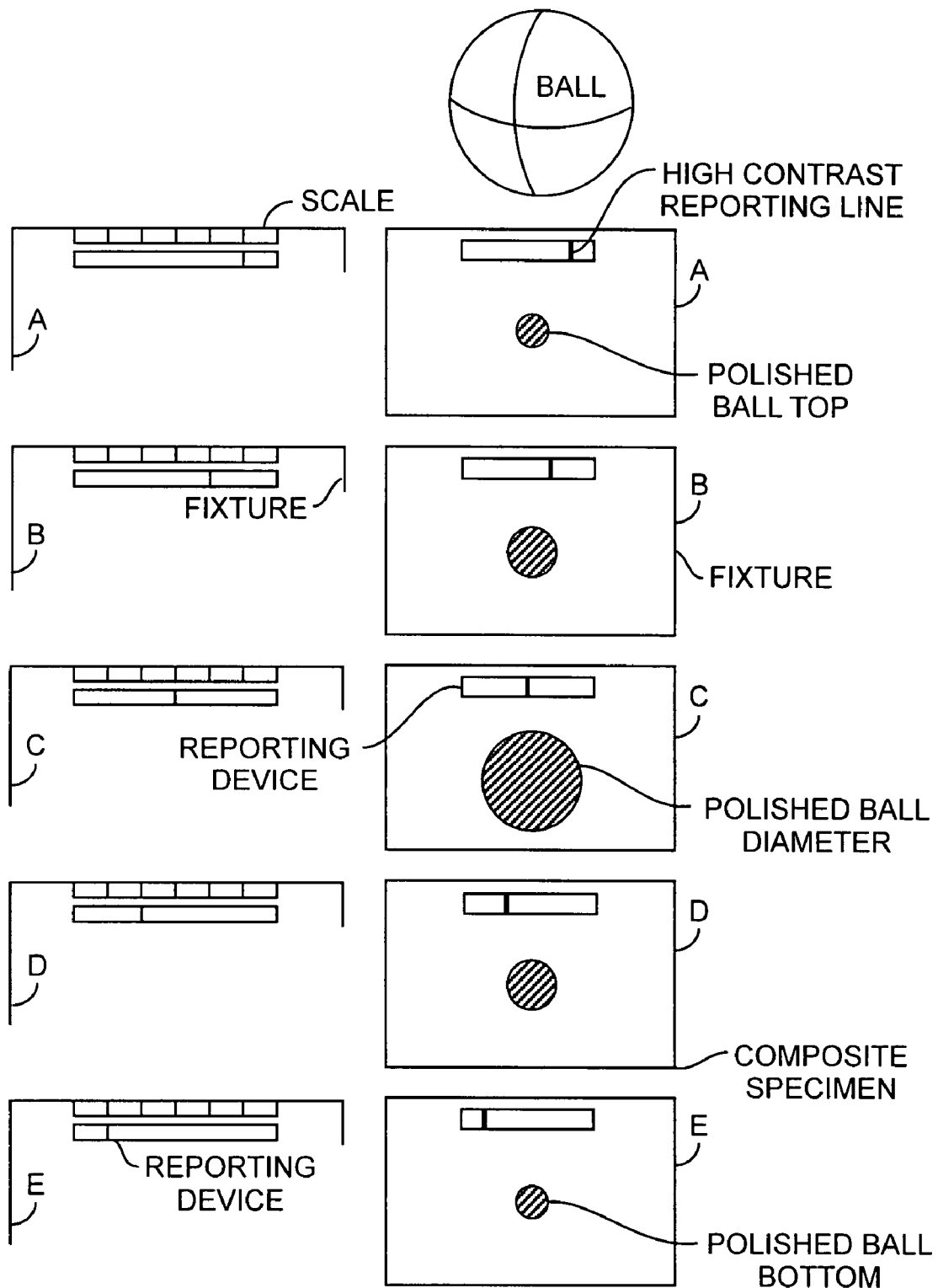
FIG. 4 shows a process flow of a reporting tomography process.

Referring to all of the Figures, and more particularly to FIG. 4, a ball is used as an exemplar object. The composite specimen comprising the object and the reporting device is a rigidly fixed robotic lifter. The specimen preferably has a base, such as a square base, upon which is rigidly affixed and disposed the object and reporting device colocated in depth and juxtaposed in plane. As the object, that is the ball, is ground, so is the reporting device. At sectioning depth A, the reporting line is far right of center and the imaged surface of the ball appears as a tiny circle. At sectioning depth B, the reporting line is right of center and the imaged surface of the ball appears as a small circle. At sectioning depth C, the reporting line is centered and the ball imaged surface appears as a circle equaling the diameter of the ball indicating a mid point through the grinding of the ball. At sectioning depth D, the reporting line is left of center and the ball imaged surface appears again as a small circle. At sectioning depth D, the reporting line is far left of center and the ball imaged surface appears again as a tiny circle. Etching sectioning represents an amount of grinding of the reporting tool and object. Any number of sectioned images at respective depths can be made at the imaging station.

The reporting device images enables automation of the sectioning process to generate tomographic datasets. Sectioning is a discrete operation to remove a depth of material, preferably in a serial manner, and more preferably with the plane of all sections lying parallel to one another. Sectioning includes, but is not limited to cutting, slicing, grinding, lapping, polishing, finishing, and nanofinishing. Sectioning may be undertaken for several purposes, for example, to remove materials to reveal a particular feature or location inside the object. Another example would be in the process of mechanical tomography, in which images of numerous sections of an object are taken in a serial manner, and are later processed to result in a three-dimensional computer reconstruction of the object.

The preferred embodiment of the reporting device comprises a block of material, which is a preferably thin layer forming the film. The film is preferably chosen to be one, which will yield a very high contrast difference from the first material when imaged. In a preferred embodiment, a thick piece of the block material is situated on top of the high-contrast layer to make a sandwich structure, which facilitates handling without contaminating the film. In cases where the mounting fixture base plate surface is parallel to the sectioning plane, the bottom surface is preferably ground or lapped to be roughly planar, and to be inclined slightly at a known angle to the plane of the high-contrast film. As material of the object and material of the reporting device are ground away, images of the sectioned surface are acquired, preferably automatically. In these images, a preferably thin high-contrast marker appears as a narrow vertical reporting line. This narrow reporting line progresses across the reporting device as well as the images as sectioning continues. The relative plane position of the line corresponds linearly with the depth of polishing, which has been performed.

In order to use the reporting device during the sectioning of an object, the reporting device must be affixed to the mounting fixture or base plate for supporting the device and object. Grinding is used to remove material, so the surfaces of the mounting base plate are oriented parallel to the sectioning plane through the device and object. The bottom surface of the reporting device, ground at the known predetermined angle, such as 30°, is facing upon the surface of the mounting fixture base plate. In this configuration, the high-contrast film is oriented with a known inclination to the sectioning plane. Thus, measurement of the depth of a given section is measurable directly from an image of the object being sectioned. A linear scale, not shown, can be added to the imaging subsystem and juxtaposed to the reporting device. Upon direct visual inspection of an image, by a human eye or an optical camera, the depth can be readily determined at the end of any sectioning step through a side by side comparison of the reporting line vis-a-vis the juxtaposed scale. Computer edge-detection algorithms are used to determine the depth from the position of the line formed by the high-contrast layer of the reporting device with high accuracy, beyond that possible with visual scales alone.

Deviation of the accuracy of the grinding is not significantly affected by variation from the desired angle between the plane of the high-contrast film and the sectioning plane. Corrections for variations in the mounting are possible at any point during the sectioning process or at any point after the sectioning process. Such misalignment can be caused by any number of factors, such as uneven glue lines in the case of wax or glue-type mounting, or by debris present on the surface of the mounting fixture, or by uneven mechanical mounting of the reporting device. To precisely calibrate the angle of inclination of the high-contrast film of the reporting device, the depth of any two sections is measured by a second method, such as a direct mechanical measurement. Precision is increased through the selection of two planes that are widely separated. Such a measurement would correspond to measuring the difference between sectioning planes A and E. These depth values, as well as the value of the position of the high-contrast reporting lines in section images, are used to calculate the angle more precisely. The position of the high-contrast reporting line in images is linearly correlated to the depth of any given section plane. Alternatively, reference features located at known depths can be used to obtain calibration information. In a preferred implementation, calibration data can be entered into the control software of the tomography system that calculates the necessary values automatically. In many cases, precise knowledge of the section depth may not be required during sectioning, and in those cases the lower-precision value from the mechanical angle of the high-contrast film is sufficient.

The materials used to fabricate the reporting device should be soft in comparison to the object being sectioned. A preferred material for the device block material is silicon. Silicon pieces with planar surfaces of high smoothness can be readily obtained. The material used to fabricate the high-contrast film is preferably a metal, and also preferably remains brightly reflecting without being tarnished, such as with a noble metal. Preferably platinum is used as the film material, but palladium, silver, and gold can also be used as well. Other exotic metals may be more inexpensive, but should also have bright and reflective properties. Most preferably, a metal that is bright and reflecting in appearance when sectioned and is inexpensive, and which has good adhesion to the block material of the device. These preferable metals may include nickel and chromium. Other preferable materials are transition metals.

The angle of inclination of the high-contrast film to the sectioning plane determines the appearance of the high-contrast reporting line in the images. The angle of the high-contrast film of the reporting device need not be perfectly aligned to a particular angle, because the exact angle can be measured from beginning and ending images of a series, with a linear relation of sections within or without a calibration region. It may be desirable to mass fabricate a set of reporting devices having a range of inclinations and reflective properties available to users.

Any type of system useful for imaging sections can be used to acquire the images. The most common example is optical microscopy. Surface treatments of the sectioned surfaces are also possible. For example, selective etches can reveal grain boundaries, damaged areas, or voids. Contrast agents can be used to highlight desired detail of objects to be sectioned. Other optical contrast mechanisms, such as luminescence or polarization, can be used. Other imaging methods besides those that sense photons may also be of use in acquiring images. Various imaging techniques could be used. In some cases, however, it may be necessary to choose a material for the high-contrast film that is not a bright reflecting metal, depending on the contrast mechanism used for the image acquisition means employed.

In an exemplar use, a turbine blade, not shown, which is to be sectioned to generate a tomographic data set for reconstruction, may reveal the shape of a failure crack in the device. The area of interest of this object measures 3 cm across and 2 cm in thickness. A reporting device with an angle of 34° and measuring 3 cm in width is used. The high-contrast film of the reporting device is composed of nickel with a thickness of one micron. Thus, the high-contrast film will appear as a line being 1.5 micron in width in all images of the object. The line will shift progressively across the frame of images taken successively during the sectioning procedure, yielding a resolution in the measurement of the depth that is limited only by the lateral resolution of the images. A common four-megapixel camera may be used for image acquisition, so the depth of sectioning is measurable with a resolution of ten microns. Although this is lower than the limits for accurate mechanical measurement of depth, utility is increased through automation.

In another exemplar use, the morphology of a weld joint is of interest. The object is five millimeters in width, and three millimeters thick. The reporting device has an angle of inclination to the sectioning plane of 5.7° and a high-contrast film of 100 nm in thickness. An imaging apparatus that yields an image 5000 pixels in width is used. The high-contrast marker is one-micron wide in images. The resolution in the measurement of the depth of sections is 0.6 microns, better than that achievable by mechanical measurement.

In yet another exemplar use, an electronic circuit board is analyzed. The region of interest is five microns thick, and ten millimeters in width. A reporting device is 10 mm wide, has an angle of inclination of 0.3°, and has a platinum high-contrast film 50 nm in thickness. The reporting line is 100 nanometers wide in captured images, which is due to the reflective nature of the film and is resolvable as a feature by the automated edge-detection algorithm under conventional control software. The resolution of depth measurements in this example, with an ordinary four-megapixel camera, is 2.5 nm.

In the preferred form, the reporting device has a flat film in horizontal relation to a linearly inclining bottom surface for creating a linear relationship between the position of the reporting line on the reporting device and the sectioning depth. The juxtaposed inspection scale would be linear as well. However, other relationships could be used, for example, polynomial, nonlinear, and logarithmic relationships could be used. For a log relationship, the bottom incline surface relative to the film would have a log relationship along the width of the device such that the position of the reporting line moves at a rate of the Log of the depth. In such a case, the juxtaposed inspection scale would be a log scale. Many relationships and scales can be used so long as the reporting line moves in one direction, and does not retrograde in movement, along and across an exposed surface of the ground reporting device while in relation to the depth of sectioning of the object.

The invention enables depth measurement directly from images taken at intervals of an object undergoing sectioning. The reporting device is preferably a planar, high-contrast layer or film that is situated adjacent to the material to be sectioned, on the mounting fixtures used in a sectioning system, with the planar, high-contrast layer oriented at a preferred incline relative to the plane of sectioning. Positions of the reporting line of the high-contrast layer will be visible in images taken at successive stages of the sectioning procedure. The depth value of the reporting line, that is, reporting marker, should be measured at least once near the beginning and near the end of the sectioning procedure for calibration. These depth values are correlated to the position of the marker in the corresponding images, yielding a linear lookup table usable for automated depth determination of each sectioning step. Thus, an accurate depth value is obtained for every image of the sectioning series. The marker is further useful for automated control of the sectioning rate by incorporation with the imaging and computer control system of an automated sectioning or automated tomography system. Visual scales can also be used for further inspections.

The reporting device can be integrated into existing automated sectioning apparatus, particularly those with automated, intermittent imaging. Measurement of the depth is directly from images of the object being sectioned. The reporting device can be integrated with conventional sectioning equipment. The device is useful for semiconductor device analysis, macro device failure analysis, manufacturing quality control, and reverse engineering. The device enables tomography of objects from objects up to at least 30 mm wide by 10 mm thick, to objects at least as small as 30 microns wide by one micron thick. While various reporting devices can be made, with various materials, shapes, and sizes, there is a relationship between the nonretrograde moving reporting line moving across the reporting device as the depth of sectioning proceeds.

As may now be apparent, the film could be a plurality of films, such as a plurality of parallel films disposed at different depths within the reporting tool for providing respective reporting lines. A plurality of reporting lines can be moving across the tool surface synchronously during grinding. Differences in separations between adjacent reporting lines indicate a planar tilt angle of grinding. Changes in the differences of the separations between the reporting lines during grinding indicate grinding tilt angle changes in the planar grinding during grinding. Changes in the angular orientations of the reporting line further indicate changes in the grinding tilt angle during grinding. Any number of films at various depths in the reporting tool could be used. The film could also comprise a plurality of parallel straight horizontal lines also disposed at different sectioning depths in the reporting tool for generating respective dots when the lines are exposed on the surface of the reporting tool during grinding. These dots serve as image references for imaging alignment when the dots are moving across the surface of the reporting during grinding. Differences in the relative locations between the dots indicate a grinding tilt angle. Changes in the differences between the locations of the dots indicate changes in the grinding tilt angle. Alternatively, inclined vertical via lines could be used in the tool so that the dots remain stationary on the reporting tool exposed surface during grinding. These dots form stationary image references. The reporting device can also provide data, which is useful for correction of a slight curvature of the ground surface of specimens. The curvature sometimes results when very wide areas are ground in small increments because the reporting line in images proceeds across the image area in correspondence with the local area removed. Any such curvature can also be measured and compensated by the use of multiple reporting devices placed in a widely separated manner. For example, multiple reporting devices can be placed on opposing sides of a specimen, or at orthogonal orientations with respect to the imaging axis, to provide a multiple series of depth measurements in correspondence with locations relative to the specimen at any given point in the grinding operation. Correction of this curvature by computer manipulation of the 3D data set further increases the accuracy of depth information across the entire field of the area imaged. As may now be apparent, the reporting tool could comprise any number of disposed films providing respective reporting lines, and any number of disposed lines providing respective reporting dots, the lines and dots for indicating various sectioning depth, image references, and grinding tilt angles. Those skilled in the art can make enhancements, improvements, and modifications to the invention, and these enhancements, improvements, and modifications may nonetheless fall within the spirit and scope of the following claims.

What is claimed is:

1. A system for grinding an object to a depth, the system comprising,
   a grinder for grinding,
   an object being ground by the grinder to the depth,
   a device having a device material with a marker material disposed therein, the device having a bottom surface and having a top surface, the grinder for grinding the top surface into a ground top surface, the marker material being disposed between the ground top surface and the bottom surface during the grinding, the marker material of the device being colocated in depth, the device being juxtaposed to the object, the marker material being exposed in part as a marker on a ground top surface of the device as the device material is ground while the object is being ground, the exposed portion of the marker material being the marker, the exposed portion of the marker being visible on the ground top surface, the bottom surface and the marker material being separated in distance by the device material for defining a relationship for indicating the depth of grinding, the relationship being between a marker position of the exposed portion of the marker material for indicating the depth of the grinding, the marker position on the ground top surface moving across the ground top surface of the device as the device material and the marker material and object are concurrently ground by the grinder, the movement of the marker across the ground top surface of the device as the device and object are being ground defining the relationship between the depth of the grinding and the position of the marker on the ground top surface, and
   a fixture for rigidly securing the device and object in the colocated and juxtaposed positions during grinding.

2. The system of claim 1 wherein,
   the movement is a nonretrograde movement.

3. The system of claim 1 wherein, the system is a tomography system, the system further comprising,
   an imaging station for inspection of the device and object, the imaging station serving to capture an image of the device and object, the image including the marker at the marker position on the ground top surface for indicating the depth of grinding.

4. The system of claim 1 wherein, the system is a tomography system, the system further comprising,
   an imaging station for inspection of the device and object, the imaging station serving to capture an image of the device and object, the image including the marker at the marker position on the ground top surface for indicating the depth of grinding, the grinding by the grinder and the imaging by the imaging station being repeated for generating a three dimensional data set of the object.

5. The system of claim 1 wherein, the system is a tomography system, the system further comprising,
   an imaging station for inspection of the device and object, the imaging station serving to capture an image of the device and object, the image including the marker at the marker position on the ground top surface for indicating the depth of grinding,
   a grinding station comprising the grinder, and
   a robot for moving the fixture between the grinder station and the imaging station.

6. The system of claim 1 wherein, the system is a tomography system, the system further comprising,
   an imaging station for inspection of the device and object, the imaging station serving to capture an image of the device and object, the image including the marker at the marker position on the ground top surface for indicating the depth of grinding,
   a grinding station comprising the grinder, the grinder being an abrasive grinder, and
   a robot for moving the fixture between the grinder station and the imaging station.

7. The system of claim 1 wherein, the system is a tomography system, the system further comprising,
   an imaging station for inspection of the device and object, the imaging station serving to capture an image of the device and object, the image including the marker at the marker position on the ground top surface for indicating the depth of grinding,
   a grinding station comprising the grinder, the grinder being an abrasive grinder,
   a wash station for washing the object and device for improved imaging, and
   a robot for moving the fixture between the grinder station and the imaging station and the wash station.

8. The system of claim 1 wherein, the system is a tomography system, the system further comprising,
   an imaging station for inspection of the device and object, the imaging station serving to capture an image of the device and object, the image including the marker at the marker position on the ground top surface for indicating the depth of grinding, a plurality of grinding stations comprising respective grinders, the grinders being abrasive grinders providing coarse and fine grinding, a wash station for washing and etching the object and device for improved imaging, and a robot for moving the fixture between the grinder station and the imaging station and the wash station.

9. The system of claim 1 wherein, the object and device are rigidly affixed to each other as a specimen.

10. The system of claim 1 wherein, the relationship is selected from the group consisting of linear, logarithmic, nonlinear, and polynomial relationships.

11. The system of claim 1 wherein, the fixture has a scale juxtaposed to the device, the scale directly indicating the depth through alignment of the marker to the scale.

12. The system of claim 1 wherein, the marker material is a horizontal planar film disposed relative to a vertical dimension in depth, the bottom surface is a linear inclined bottom surface, and the relationship is a linear relationship.

13. The system of claim 1 wherein, the marker material is a horizontal planar film disposed relative to a vertical dimension in depth, the bottom surface is a machined linear inclined bottom surface, and the relationship is a linear relationship.

14. The system of claim 1 wherein, the marker material is a metal.

15. The system of claim 1 wherein, the marker material is selected from the group consisting of platinum, palladium, silver, gold, chrome, and nickel.

16. The system of claim 1 wherein, the device has a top portion and a bottom portion between which is disposed the maker material, the object comprising an object material, the top portion and bottom portion are made of the device material, and the device material is softer than the object material.

* * * * *